(12) United States Patent
Shetty et al.

(10) Patent No.: US 8,758,447 B2
(45) Date of Patent: Jun. 24, 2014

(54) DEVICE AND METHOD FOR REPAIR OF UROLOGICAL STRUCTURES

(75) Inventors: Dhanuraj S. Shetty, Jersey City, NJ (US); Jackie J. Donners, West Windsor, NJ (US); Sridevi Dhanaraj, Raritan, NJ (US); Jeffrey C. Geesin, Doylestown, PA (US)

(73) Assignee: Ethicon, Inc., Somerville, NJ (US)

( * ) Notice: Subject to any disclaimer, the term of this patent is extended or adjusted under 35 U.S.C. 154(b) by 879 days.

(21) Appl. No.: 12/494,887

(22) Filed: Jun. 30, 2009

(65) Prior Publication Data

US 2010/0331864 A1 Dec. 30, 2010

(51) Int. Cl.
*A61F 2/04* (2013.01)
*A61L 27/58* (2006.01)
*A61L 27/48* (2006.01)

(52) U.S. Cl.
CPC ............ *A61L 27/58* (2013.01); *A61L 2430/22* (2013.01); *A71L 27/18* (2013.01); *A61L 27/48* (2013.01)
USPC ...................................................... 623/23.65

(58) Field of Classification Search
USPC ...................... 623/23.65, 23.66, 23.72, 23.74; 606/151, 213; 600/29–31, 37; 128/869, 128/885–887, 898
See application file for complete search history.

(56) References Cited

U.S. PATENT DOCUMENTS

| | | | |
|---|---|---|---|
| 5,840,011 A | 11/1998 | Landgrebe et al. | |
| 6,147,135 A | 11/2000 | Yuan | |
| 6,309,423 B2 | 10/2001 | Hayes | |
| 6,486,377 B2 | 11/2002 | Rapp | |
| 6,576,019 B1 | 6/2003 | Atala | |
| 7,297,102 B2 | 11/2007 | Smith | |
| 8,197,837 B2 | 6/2012 | Jamiolkowski | |
| 2006/0002972 A1 | 1/2006 | Atala | |
| 2006/0229596 A1* | 10/2006 | Weiser et al. | 606/37 |
| 2007/0036842 A1 | 2/2007 | Spencer | |
| 2007/0275363 A1 | 11/2007 | Bertram et al. | |
| 2007/0276507 A1* | 11/2007 | Bertram et al. | 623/23.65 |
| 2008/0319460 A1* | 12/2008 | Cortellini | 606/151 |
| 2010/0152530 A1 | 6/2010 | Timmer | |
| 2010/0331963 A1 | 12/2010 | Donners | |

FOREIGN PATENT DOCUMENTS

| | | |
|---|---|---|
| GB | 2222954 A | 3/1990 |
| WO | 2006019600 A2 | 2/2006 |
| WO | 2007132186 A2 | 11/2007 |

OTHER PUBLICATIONS

Atala, et al. "Formation of Urothelial Structures in vivo from Dissociated Cells Attached to Biodegradable Polymer Scaffolds in Viva", J. Urol., part 1, 148:658 (1992).
Oberpenning et al., "De Novo Reconsitution of a Functional Mammaliam Urinary Bladder by Tissue Engineering", Nature Biotechnology, vol. 17, pp. 149-155, Feb. 1999.
Vacanti, et al. "Selective Cell Transplantation Using Bioabsorbable Artificial Polymers as Matrices", J. Pediatr. Surg. 23:3-9, 1988.

\* cited by examiner

*Primary Examiner* — Melanie Tyson

(57) ABSTRACT

A tissue engineering construct made from a nonwoven fabric. The fabric is made from first and second staple fibers. The first staple fibers are made from a first biocompatible, bioabsorbable material, and the second staple fibers are made from a second biocompatible, bioabsorbable material. The first material has a melting temperature lower than the second material. The fabric is formed into a three-dimensional construct suitable for the repair of urinary tract structures.

5 Claims, 5 Drawing Sheets

DEVICE AND METHOD FOR REPAIR OF UROLOGICAL STRUCTURES

CROSS-REFERENCE TO RELATED APPLICATIONS

This application is related to commonly assigned patent application Ser. No. 12/495,001 filed on evendate herewith, which is incorporated by reference

FIELD OF THE INVENTION

The present invention relates to nonwoven scaffolds for the augmentation, reconstruction, and repair of hollow organs, including lower urological structures such as the urinary bladder.

BACKGROUND OF THE INVENTION

Currently and traditionally, defects in the bladder and other urothelial structures have been corrected surgically following cystectomy procedures. Some of the closure techniques following cystectomy involve auto augmentation for closure of the opening for which there is insufficient tissue or when the structure itself is deformed or too small to have complete closure and sufficient regeneration. The gold standard for the reconstruction of the bladder is enterocystoplasty, a procedure that uses intestinal bowel segments, however, this procedure is associated with several complications. Bowel segments have been used in reconstruction of genitourinary structures in these circumstances. The use of bowel in genitourinary reconstruction is associated with a variety of complications, including metabolic abnormalities, infection, perforation, urolithiasis, increased mucus production and malignancy.

Several materials, both absorbable and synthetic, have been used unsuccessfully as substitutes for the bowel segment in this reconstruction process for bladder repair/augmentation and regeneration. However no material has proven to be an ideal biomaterial for bladder reconstruction. Synthetic materials such as polyvinyl sponge, gelatin sponge, polytetrafluoroethylene, and silicon have been used unsuccessfully due to mechanical, structural or biocompatibility issues. Naturally derived materials such as dura, de-epithelialized bowel segment, omentum, peritoneum, seromuscular grafts, and small intestinal submucosa (SIS) have also been evaluated for bladder repair and replacement with limited success.

Recent studies indicate that the biodegradable polyester polymers made of polyglycolic acid are useful for bladder repair and reconstruction, as described by Vacanti, et al Selective cell transplantation using bioabsorbable artificial polymers as matrices. *J. Pediatr Surg* 23:3-9. 1988. Furthermore, the feasibility of using biodegradable polymers as delivery vehicles for urothelial cell transplantation has been demonstrated by studies showing that urothelial cells will adhere to synthetic polymers composed of polyglycolic acid and survive in vivo, as reported by Atala, et al., "Formation of urothelial structures in vivo from dissociated cells attached to biodegradable polymer scaffolds in vivo", *J. Urol.*, part 1, 148: 658 (1992). However, this process is long and time consuming where a patient has to wait for at least eight weeks before the next implantation of a tissue engineered scaffold.

Tissue engineering based approaches, such as the cell culturing based technology (Oberpenning, et al. De novo reconstitution of a functional mammalian urinary bladder by tissue engineering. *Nature Biotechnology Vol.* 17 February 1999), has described the use of poly(glycolic acid) (PGA) scaffold for the reconstruction of the urinary bladder. Oberpenning, et al. compares the usefulness of synthetic polymer matrices in the absence (acellular group) and the presence of seeded cells (cellular group) for bladder reconstruction. In the study urothelial and smooth muscle cells were harvested, cultured and seeded on PGA nonwoven scaffold, were implanted in a beagle dog following partial cystectomy and evaluated over 11 months. The acellular group animal, at the end of the 6-month time frame, did not show any increase in the bladder capacity as compared to its baseline (precystectomy) volume and at the end of the 11 month time frame, the acellular group still did not reach its baseline capacity. Whereas in the cellular group at the end of 6 months, the bladder capacity almost reached its baseline capacity and at the end of 11 months the cellular group was able to approach and just surpass its pre-cystectomy bladder capacity or volume. The results of the changes in the bladder capacity from this study are highlighted in FIG. 1. Some of the results from this study have been published in U.S. Pat. No. 6,576,019.

One significant limitation from the above study was that there was no significant increase in the bladder capacity over the precystectomy values, for both the groups at the end of 6 and 11 months. This could be a huge implication for neurogenic bladder patients, where there is always a need for an increased bladder capacity.

Therefore, there is a need in this art for novel scaffolds for correcting bladder defects, which do not require obtaining and implanting cells on the polymer scaffold.

SUMMARY OF THE INVENTION

Accordingly, novel devices s for correcting defects in or problems with the urinary structure, including bladder defects, are disclosed. The scaffolds are in the form of an acellular device for urological repair having a nonwoven fabric that has at least a first biocompatible, bioabsorbable material and a second biocompatible, bioabsorbable material, where the first biocompatible bioabsorbable material is poly (p-dioxanone).

Another aspect of the present invention is a method of repairing a urinary structure using such devices.

These embodiments and other advantages of the present invention will become more apparent from the following description and accompanying drawings.

DETAILED DESCRIPTION OF THE INVENTION

Figure 1:
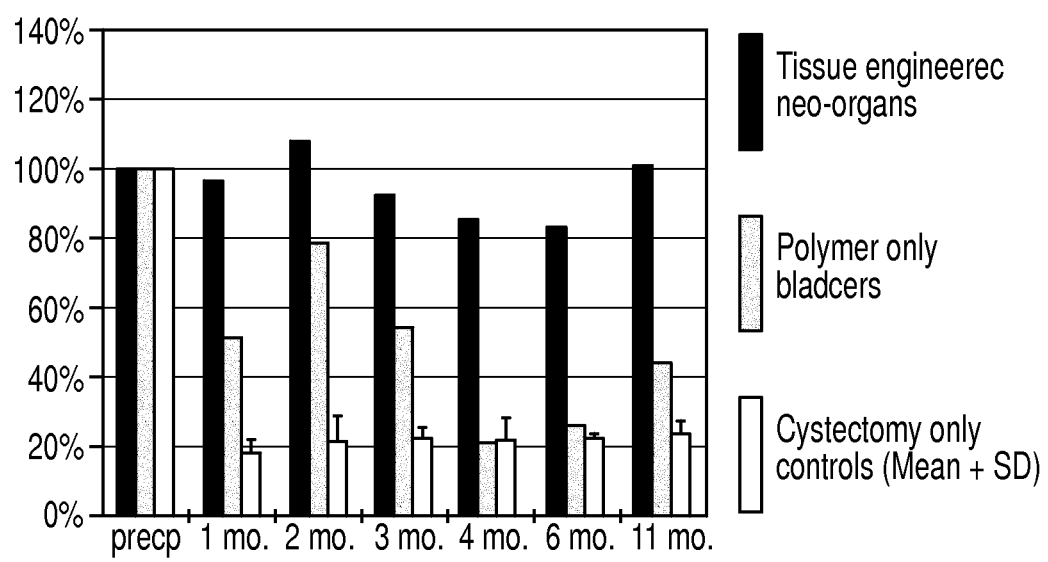
FIG. 1 is a graph showing a prior art study of Bladder Capacity of Beagle dogs from a published paper (Oberpenning et al.)

As used herein the term "acellular device" means that the device is provided without the seeding of cells, minced tissue, or any other cell containing tissue.

As used herein the term "urological repair" means the repair, augmentation or reconstruction of urological structures such as, the bladder, the ureters and the urethra.

As used herein, the term "nonwoven fabric" includes bonded fabrics, formed fabrics, or engineered fabrics, and the like that are manufactured by processes other than weaving or knitting. More specifically, the term "nonwoven fabric" refers to a porous, textile-like material, usually in flat sheet form, composed primarily or entirely of staple fibers assembled in a web, sheet or batt. For the purposes of this invention, staple fibers are cut to a specific length from the continuous filament fiber. Usually the staple fiber is cut to length in the range of about 1.5 inches to about 8 inches. The structure of the nonwoven fabric is based on the arrangement of the staple fibers that are typically arranged more or less randomly. The tensile, stress-strain and tactile properties of the nonwoven fabric ordinarily stem from fiber to fiber friction created by entanglement and reinforcement of, for example, staple fibers, and/or from adhesive, chemical or physical bonding. Notwithstanding, the raw materials used to manufacture the nonwoven fabric may be yarns, scrims, netting, braids or filaments made by processes that include, weaving or knitting.

Preferably, the nonwoven fabric is made by processes other than, weaving or knitting. For example, the nonwoven fabric may be prepared from yarn, scrims, netting or filaments that have been made by processes that include, weaving or knitting. In the case of dry laid nonwoven process, the yarn, scrims, netting and/or filaments are crimped to enhance entanglement with each other and attachment to the second absorbable woven or knitted fabric. Such crimped yarn, scrims, netting and/or filaments may then be cut into staple fibers that is long enough to entangle. The staple fibers may be between about 0.1 and 3.0 inches long, preferably between about 0.75 and 2.5 inches, and most preferably between about 1.5 and 2.0 inches. In one embodiment, the staple fiber length is about 2 inches. The staple may be carded, wet laid, or air laid to create a nonwoven batt, which may be then calendared, needlepunched, hydroentangled, or air entangled into the nonwoven fabric. Additionally, the staple may be kinked or piled. Other methods known in the art for the production of nonwoven fabrics may be utilized.

In one embodiment, the nonwoven fabric has a thickness in the range of about 0.5 mm to about 5 mm. In another embodiment, the nowoven fabric has a thickness in the range of about 0.5 mm-to about 2 mm. In one embodiment, the nonwoven fabric has a density in the range of about 60 mg/cc-about 300 mg/cc. In another embodiment the nonwoven fabric has a density in the range of about 60-120 mg/cc.

The staple fibers are comprised of biocompatible, bioabsorbable materials including, but not limited to aliphatic polyester polymers, copolymers, or blends thereof. The aliphatic polyesters are typically synthesized in a ring opening polymerization of monomers including, but not limited to, lactide (including L-, D-, meso and D, L mixtures and lactic acid), glycolide (including glycolic acid), epsilon-caprolactone, p-dioxanone (1,4-dioxan-2-one), and trimethylene carbonate (1,3-dioxan-2-one).

In one embodiment, the staple fibers are comprised of at least a first biocompatible, bioabsorbable material and a second biocompatible, bioabsorbable material, where the first biocompatible, bioabsorbable material is poly(p-dioxanone). In one embodiment, the second biocompatible, bioabsorbable material is selected from the group consisting of poly (glycolide-co-epsilon-caprolactone) having a molar ratio of glycolide to epsilon-caprolactone of about 75/25; poly(glycolide); and poly(lactide-co-glycolide) having a molar ratio of lacide to glycolide of about 90/10 or about 10/90. In another embodiment, the second biocompatible, bioabsorbable material is a poly(lactide-co-glycolide) having a monomer mole ratio of 10/90 lactide/glycolide. In one embodiment, the poly(p-dioxanone) material is present in the nonwoven in the amount of about 5% to about 95% by weight. In another embodiment, the poly(p-dioxanone) material is present in the nonwoven in the amount of about 50% to about 70% by weight. In yet another embodiment, the poly(p-dioxanone) material is present in the nonwoven in the amount of about 30% by weight.

The nonwoven fabric may be formed into a suitable shape for urological repair by conventional methods such as, cutting the nonwoven fabric into a suitable design and then approximating the edges of the nonwoven to form the suitable shape, placing the fabric in a mold, and the like. Suitable designs to cut the nonwoven fabric into include but are not limited to square, rectangular, triangular, petal, and the like. For example, for bladder repair the nonwoven may be cut into a flower petal design, approximate the adjacent edges, and temporarily hold the edges together to form a hollow, sphere shaped device with an opening for attaching to the existing bladder. The edges may be secured by sewing closed with a suture, stapling, melt bonding and the like.

In one embodiment, the edges are secured by suturing followed by either dip-coating the scaffold in a polymer/solvent solution or by melt bonding to provide better structural integrity to the scaffold. For example, sutured scaffolds may be dip coated in a 5% (w/v) 50/50 poly(lactide-co-glycolide) (PLA/PGA) solution in dichloromethane (DCM) in order to impart appropriate stiffness to the woven. In another embodiment, the sutured scaffolds may be melt bonded to provide structural integrity as described below.

In another embodiment, the edges are secured and stiffness is induced in the scaffold by melt bonding. Melt bonding may be accomplished by approximating the scaffold edges, temporarily securing the edges, and at least partially melting the PDS fibers by heating to a temperature of about 105° C. to about 150° C., and then allowing to cool to room temperature. In one embodiment, the nonwoven fabric is comprised of a first biocompatible, bioabsorbable material having a first melting temperature and a second biocompatible, bioabsorbable material having a second melting temperature, where the first melting temperature is lower than the second melting temperature. The first and second melting temperatures must be sufficiently different such that upon heating to the first melting temperature the first biocompatible, bioabsorbable material is at least partially melted and the second biocompatible, bioabsorable material is not melted. By partially melted, we mean that the first material will flow and attach to the second material such that upon cooling the two materials will be bonded together.

The edges of the nonwoven may be held together by tacks, pins, clips, mechanical clamps that are designed to the contours of the overall scaffold edges, or any other device that secures the adjacent edges of the device until the heating step is completed. Heating may be accomplished using conventional heating means, such as an oven, vacuum oven, and the like. Heating may accomplished under inert atmosphere such as, under nitrogen blanket. Optionally, the adjacent edges may be further reinforced by placing a film comprising poly (p-dioxanone) between the adjacent edges such that during the next step, the heating step, the edges are attached even more securely without affecting the porosity that is necessary for cell in growth in the rest of the scaffold. The hollow organ scaffold is now in a suitable shape for hollow organ repair including, but not limited to spherical, hemispeherical, conical, prism, and cylindrical, and combinations thereof.

Figure 4:
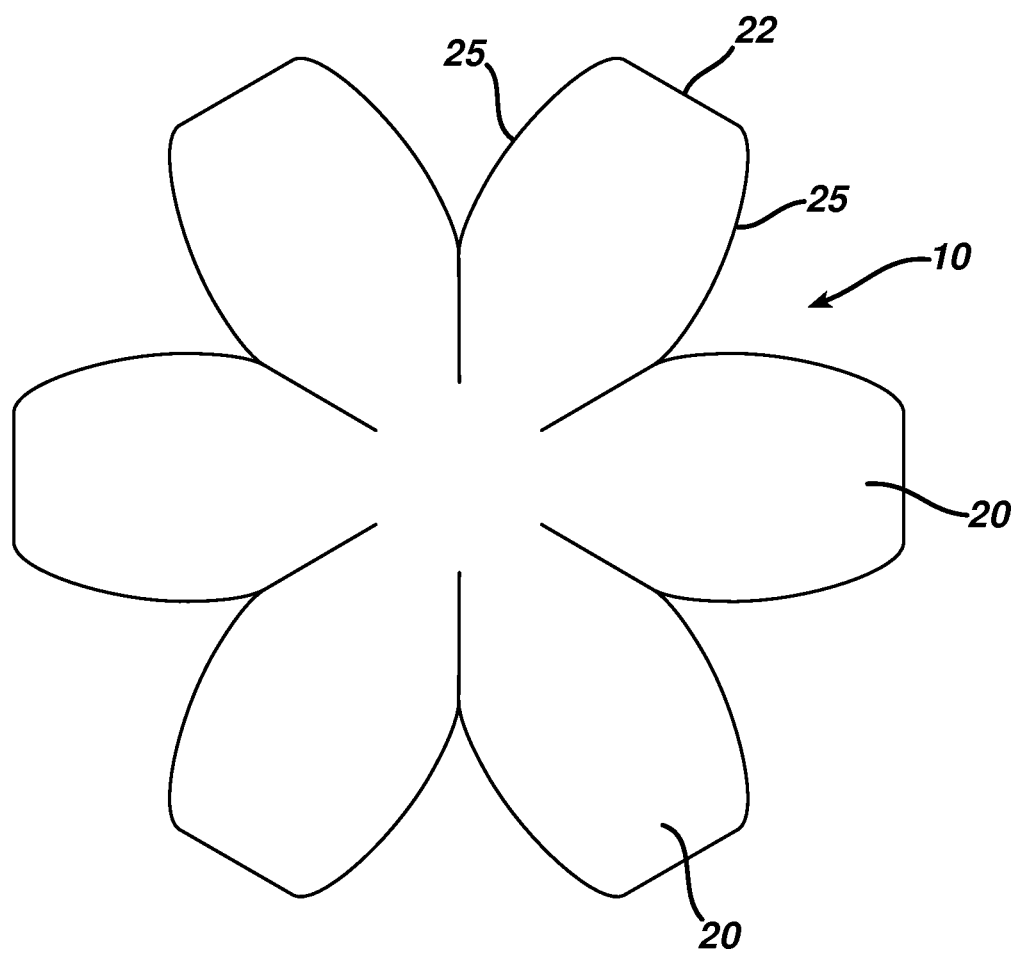
FIG. 4 is a top view of an exemplary embodiment of the petal shape for preparing the bladder repair device of the invention.
Figure 5:
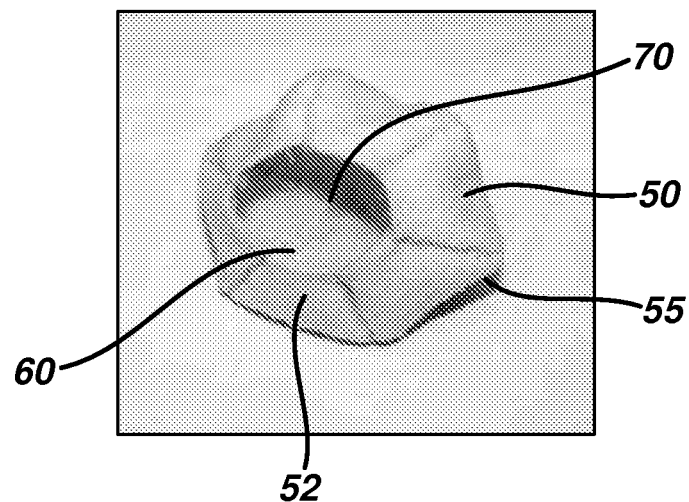
FIG. 5 is a perspective view of an exemplary embodiment of a bladder repair device of the invention.
Figure 6:
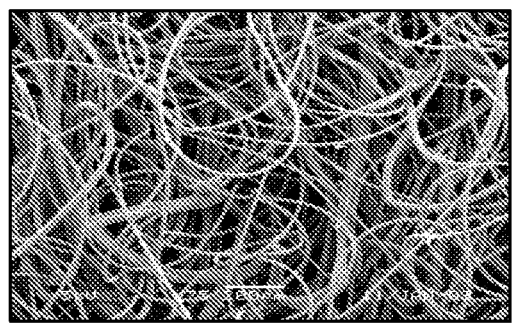
FIG. 6 is a scanning electron micrograph of a nonwoven fabric used to prepare the bladder repair device of the invention.

A suitable bladder shaped device 50 is shown in FIG. 5. Preferably, device 50 is hollow or at least partially hollow. The device 50 is seen to have opening 60 in top 52 which is in communication with inner cavity 70. The device has bottom 55. The device 50 was prepared from a dry laid nonwoven fabric 10 comprising staple fibers further comprising a ratio of 70:30 of 90/10 poly(glycolide-co-lactide)(PGA/PLA): poly(p-dioxanone) (PDS). The 90/10 PGA/PLA staple fibers have a fiber diameter of about 20 microns and the PDS staple fibers have an average fiber diameter of about 40-60 microns. The nonwoven fabric 10 was first cut into a petal shape that had six petal shaped leaves 20 having edges 25 as shown in FIG. 4. The top portion 22 of each petal leaf 20 was truncated such that after attaching the edges 25 of adjacent leaves 20 together thereby forming device 50 such that there is a single opening 60 of about 2 cm. During the surgical procedure this opening is then attached to the cystectymied bladder.

The acellular device for urological repair may be particularly useful in treating the bladder. The bladder may benefit from placement of the acellular device as a "patch" in an area requiring tissue augmentation or regeneration. For example, regarding the bladder, if an area of the bladder is missing due to congenital defect or has been lost due to disease, injury or surgery (e.g., partial cystectomy), the patient may benefit from having the bladder area increased or restored to the original size as the particulars of the case allows.

The devices of the present invention may also be suitable for repair of other hollow organs using conventional tissue engineering techniques. Such techniques include the incorporation of cells or minced tissues into the scaffold. The hollow organs that may be repaired include blood vessels, esophagus, trachea, stomach, ureters, and the urethra.

The following examples are illustrative of the principles and practice of the present invention, although not limited thereto.

Example 1

Preparation of an Acellular Scaffold for Urological Repair

Nonwovens were manufactured having staple fibers comprised of PDS and 90/10 PGA/PLA. The lot numbers and specifications for these nonwovens are tabulated in Table 1.

TABLE 1

Lot numbers and specifications of nonwovens.

| Lot number | Material Composition | Ratio (wt. %) | Density (mg/cc) | Thickness (mm) |
|---|---|---|---|---|
| MD00348-01 | (90/10 PGA/PLA)/PDS | 70/30 | 100 | 1.5 |
| MD00370-01 | (90/10 PGA/PLA)/PDS | 70/30 | 100 | 1.5 |
| MD00370-05 | (90/10 PGA/PLA)/PDS | 70/30 | 100 | 1.5 |
| MD00370-06 | (90/10 PGA/PLA)/PDS | 70/30 | 100 | 1.5 |
| MD00370-09 | (90/10 PGA/PLA)/PDS | 70/30 | 100 | 1.5 |

The nonwovens were scoured by incubating in alcohol followed by ultrapure water. Samples were subsequently dried by blotting with sterile gamma wipes, drying for 10 minutes with cold air and overnight drying under vacuum. Samples were cut into petal-shaped samples (as shown in FIG. 4) with a cutting die #31268 (DV Die, Danvers, Mass.) using a Carver 2696 laboratory press (Carver, Wabash, Ind.) at 4 tons of pressure.

Example 1A

Suture Approach

Petal-shaped samples were sutured into bladder-shaped scaffolds with 90/10 PGA/PLA suture sold under the tradename VICRYL (4-0 suture, Ethicon, Inc., Somerville, N.J., J415H, Lot # ZH6093) with an average stitch density of 17 stitches/inch and a knot at every $5^{th}$ stitch. Scaffolds were dip-coated 3 times in a 5 weight% 50/50 PLA/PGA solution (Sigma, St. Louis, Mo., P2191) in dichloromethane and air-dried in between coating steps. The dip coated scaffold was finally dried under nitrogen overnight to ensure complete removal of the dichloromethane. After the drying was completed, the scaffolds were put in a sterilization package and the scaffolds were sterilized with ethylene oxide. See FIG. 5 for an exemplary scaffold for bladder repair.

Example 1B

Melt-Bond Approach

Adjacent edges of petal-shaped samples are held together at the edges with 2 binder clips per edge to form a bladder-shaped scaffold and draped over a mold. The edges overlapped about 0.5-1 cm. Alternatively the edges can be held together with PDS films of thickness of about 0.8 mm. The sample with the edges held together are placed in heated vacuum chamber that is set to 130° C. Subsequently, the scaffold was heated to 130° C. for 5 minutes and after removal from the oven allowed to cool for 5 minutes before removing the clips. After the melt bonding process was completed, t the scaffold was put in a package and the scaffolds are sterilized with ethylene oxide.

NO

Example 2

Partial Cystectomy Procedure for Acellular Group and the Cellular Group

There were two treatment groups. In Group 1, acellular scaffolds were prepared as in Example 1A. In Group 2, cellular scaffolds were prepared as described in Example 1A and were seeded with autologous minced tissue at the time of implantation, with 6 animals per treatment group. Before anesthesia was administered, each animal was premedicated with buprenorphine (0.01 mg/kg, subcutaneously[SC]) and meloxicam (0.2 mg/kg SC). An intravenous catheter was placed in a peripheral vessel. The animals were anesthetized with Propofol (3-10 mg/kg, intravenously). To help prevent infection, the animals were given cefotaxime (50 mg/kg, IV) before surgery and again at its completion.

During the surgery, a midline incision was made in the abdomen, beginning immediately caudal to the umbilicus. The omentum was exposed in its entirety and the bladder brought through two small incisions near its caudal one-third, so that approximately one-third of the omentum came to lie caudal to the urinary bladder itself. The trigone area was identified and about 40-45% of the dome portion of the urinary bladder was removed leaving the trigone area intact. The acellular scaffold as described in Example 1A (as shown in FIG. 5) was then anastomosed to the normal urinary bladder tissue using 2.0 VICRYL suture. In addition for the cellular group, excised urinary bladder tissue was identified and aseptically transferred on a Petri dish for the preparation of the tissue and the test device in the operating room. The excised urinary bladder was weighed in a sterile manner and the measurement recorded. An 8 mm-punch biopsy was used to harvest the required amount of tissue for processing. The tissue samples were then minced using opposing scalpel blades under sterile conditions to create a suspension of autologous tissue. The minced tissue was then placed on the device prepared as described in Example 1A such that the autologous tissue suspension was evenly distributed on the scaffold in a sterile manner. In addition, approximately 4 nonabsorbable polypropylene sutures were placed in each quadrant of the device to aid in identifying the anastomotic site at the time of necropsy. A sterile staple was then attached to the suture for identification purposes for necropsy. For animals in both the groups, the omentum was then pulled over the test device and secured with fibrin glue (sold under the tradename EVICEL (Ethicon, Inc., Somerville, N.J.). The abdominal incision was closed in layers with an 2-0 suture sold under the tradename VICRYL (Ethicon, Inc., Somerville, N.J.). The catheter was left in place for a period of about 2 weeks to facilitate postoperative urine collection after device implantation.

Bladder Cycling was performed on Day 14 and Day 30 after test device implantation. Bladder Cycling is a process that is usually done post operatively, wherein saline solution is introduced into the bladder so that the bladder inflates and deflates, thereby exposing the bladder to physiological conditions for its normal development. Urodynamic measurements such as Volume and Compliance and cystograms were taken on Days 30, 60, 90, 120 and 150 days and prior to necropsy (180 days). Urodynamic Volume measurements are recorded values of the total capacity of the bladder at the point of leak. Urodynamic compliance measurements are essentially the ratio of the measured volume over measured pressure at the point of leak. Higher the compliance measurements indicate that the bladder is able to hold large amount of volumes at lower pressure. The bladder urodynamic measurements were obtained after the urinary bladder was catheterized with a dual lumen catheter. All residual urine was removed and the catheter size and placement was recorded. One lumen was connected to a direct pressure cable and the other lumen was used to infuse 0.9% sodium chloride at a rate of 10-25 mL/min. The time, pressure and the total volume was recorded at the time of leakage that was observed around the catheter. The cystograms showed no sign of abnormalities or gross leakages in all the animals.

Figure 2:
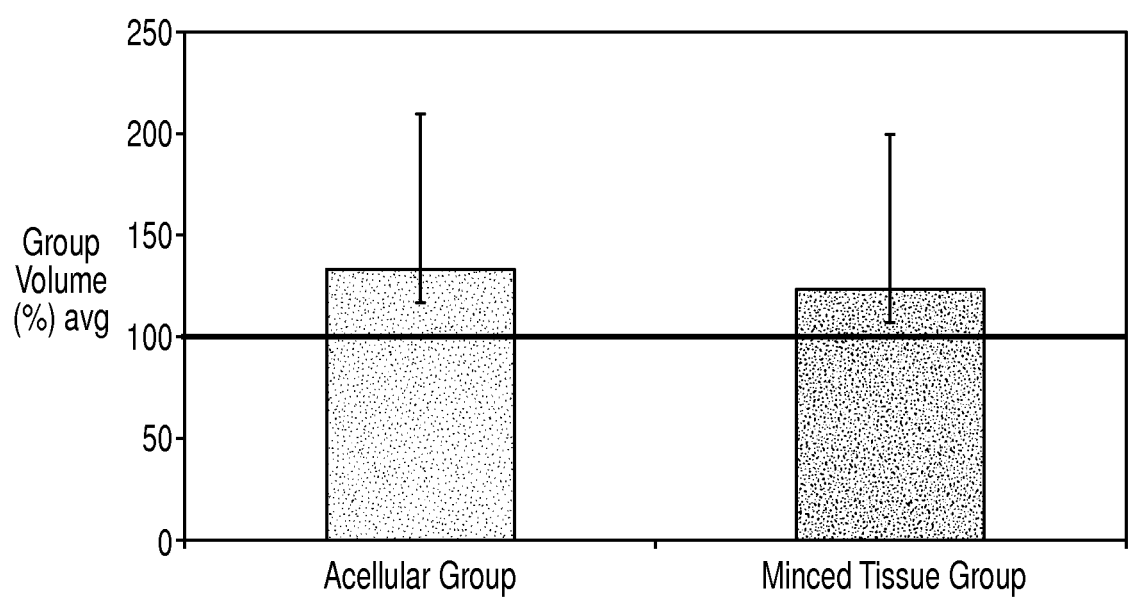
FIG. 2. is a graph showing average bladder capacity study (n=6) over six months.
Figure 3:
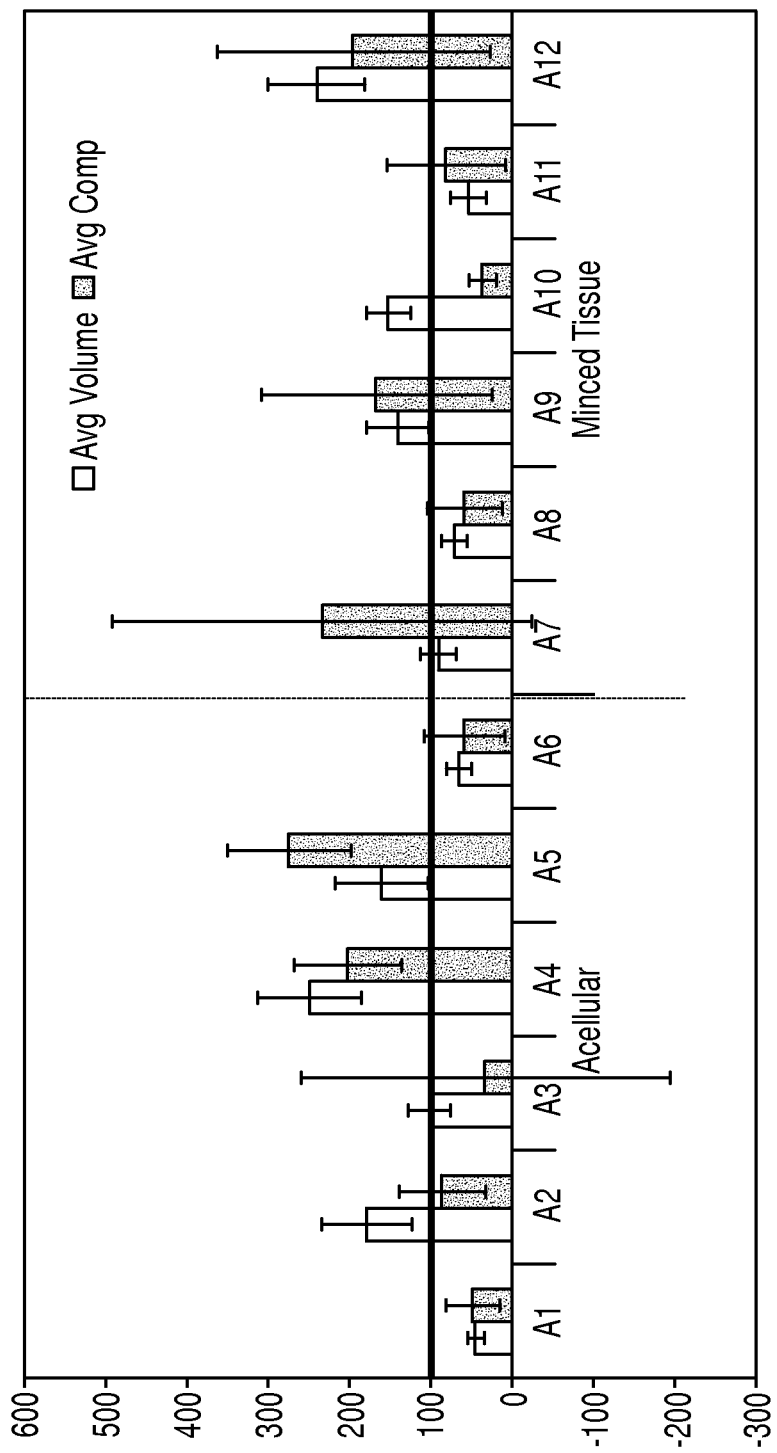
FIG. 3 is a graph of the individual bladder capacities and compliance measurements (n=6).

Urodynamic measurements and cystograms were taken every month, over a period of six (6) months. In functional evaluations for up to 6 months, the neo bladder in both the groups demonstrated an increase in bladder capacity over its precystectomy values. In some cases, for both the groups, the increase was over 100% from the precystectomy values. Specifically for the acellular group, when compared to the acellular group from the above-published paper (Oberpenning) and patent (U.S. Pat. No. 6,576,019B1), the findings from this study at the six-month time point were unexpected and significant. For the acellular group, overall a higher compliance results were observed at the end of six months indicating that the regenerated bladder was able to hold higher volumes of urine at lower pressure. The cystograms showed no sign of abnormalities or gross leakages in all the animals. The finding from our study is represented graphically in FIGS. 2 & 3. FIG. 2 shows the average bladder volume or capacity of all the animals in each group over 6 months. FIG. 3 shows the bladder volume and compliance measurements for each of the animals for both groups measured over 6 months.

Although this invention has been shown and described with respect to detailed embodiments thereof, it will be understood by those skilled in the art that various changes in form and detail thereof may be made without departing from the spirit and scope of the claimed invention.

We claim:

1. A method of repairing a urinary structure comprising the steps of:
   A. providing an acellular repair device comprising:
      a nonwoven fabric, wherein said fabric comprises first and second staple fibers,
      wherein the first staple fibers comprise a first biocompatible, bioabsorbable material and the second staple fibers comprise a second biocompatible, bioabsorbable material,
      wherein the first biocompatible bioabsorbable material is poly(p-dioxanone) and the second biocompatible material comprises a polymer selected from the group consisting of poly(glycolide) and poly(glycolide-co-lactide), and
      wherein said fabric is formed into a three-dimensional shape having an opening and an internal cavity wherein the opening is in communication with the cavity and the cavity is suitable for urinary bladder repair; and,
   B. attaching the opening on the acellular repair device to a urinary bladder structure.

2. The method of claim 1, wherein in the shape is selected from the group consisting of spheres, hemispheres, prisms, cylinders, cones, and combinations thereof.

3. The method of claim 1, wherein the nonwoven fabric comprises about 50% to about 75% by weight of the first biocompatible, bioabsorbable material.

4. The method of claim 1, wherein the first and second staple fibers have a length from about 0.75 inches to about 2.0 inches.

5. The method of claim 1, comprising the additional steps of performing a partial bladder cystectomy and attaching the urinary repair device to a remaining section of the bladder.

\* \* \* \* \*